United States Patent [19]

Cox et al.

[11] Patent Number: 4,851,419
[45] Date of Patent: Jul. 25, 1989

[54] CERTAIN 2-PYRIDINYL-PHENYLSULFINYL-BENZOXAZOLES, THE CORRESPONDING BENZOTHIAZOLES OR BENZIMIDAZOLES HAVING ANTI-INFLAMMATORY OR GASTRIC ACID SECRETION INHIBITION ACTIVITY

[75] Inventors: David Cox; David E. Hall; Anthony H. Ingall; John L. Suschitzky, all of Loughborough, England

[73] Assignee: Fisons plc, Ipswich, England

[21] Appl. No.: 918,832

[22] Filed: Oct. 14, 1986

[30] Foreign Application Priority Data

Oct. 16, 1985 [GB] United Kingdom ............... 8525452
Oct. 16, 1985 [GB] United Kingdom ............... 8525454
Sep. 10, 1986 [GB] United Kingdom ............... 8621768

[51] Int. Cl.⁴ ............... C07D 401/12; C07D 413/12; C07D 417/12; A61K 31/44
[52] U.S. Cl. ............................ 514/338; 546/270; 546/271
[58] Field of Search ............... 546/278, 270, 271; 514/338

[56] References Cited

PUBLICATIONS

Chemical Abstracts, vol. 108(11) Abst. No. 108:94553f, Mar. 14, 1988.
Chemical Abstracts, vol. 109(11), Abst. No. 109:93009s, Sep. 12, 1988.

*Primary Examiner*—Alan L. Rotman
*Attorney, Agent, or Firm*—Marshall, O'Toole, Gerstein, Murray & Bicknell

[57] ABSTRACT

There are described compounds of formula I,

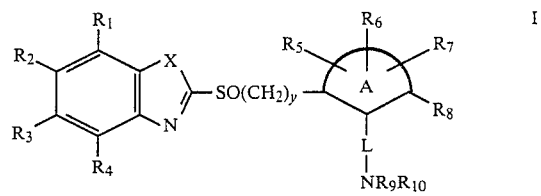

in which A is a benzene or heterocyclic ring,
y is 0 or 1,
L is a group containing 1 or 2 carbon atoms, or is a single bond,
$R_9$ and $R_{10}$ have a variety of significances, e.g.
$R_{10}$ may form part of a double bond with L, or
the group —$NR_9R_{10}$ forms a ring carrying substituents $R_1$ and $R_8$, or
when L is a single bond —$NR_{10}$ and $R_8$ may form a ring carrying substituents $R_{16}$ to $R_{25}$, or
the group —$LNR_9R_{10}$ forms a heterocyclic ring carrying substituents $R_{26}$ to $R_{33}$,
$R_1$ to $R_8$ and $R_{16}$ to $R_{33}$ have a variety of significances
n is 0, 1 or 2,
x is 3, 4 or 5,
X is S, O or $NR_{15}$,
$R_{15}$ is hydrogen, —COR, —COOR or alkyl optionally substituted by —OCOR,
and certain provisos.

Processes for making the compounds and pharmaceutical formulations containing them, e.g. for the treatment of conditions involving excess gastric acid secretion, are also described.

6 Claims, No Drawings

CERTAIN 2-PYRIDINYL-PHENYLSULFINYL-BENZOXAZOLES, THE CORRESPONDING BENZOTHIAZOLES OR BENZIMIDAZOLES HAVING ANTI-INFLAMMATORY OR GASTRIC ACID SECRETION INHIBITION ACTIVITY

This invention relates to new compounds, methods for their preparation and pharmaceutical formulations containing them.

A number of 2-(pyridylmethylsulphinyl) benzimidazoles are known for use as pharmaceuticals from European Patent Applications Nos. 5129 and 80602 and from British Patent Application No. 2,134,523. A number of 2-(heterocyclimethylsulphinyl)benzimidazoles are known from West German OLS No. 2,548,340 and French Patent No. 2,392,021.

We have now found a novel group of benzimidazoles, benzoxazoles and benzothiazoles which have pharmacological activity.

According to the invention we provide compounds of formula I,

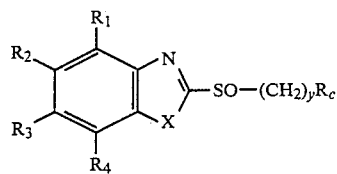

wherein $R_c$ represents a ring of formula II,

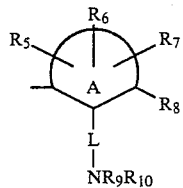

in which A represents a benzene ring, or a 5 or 6 membered nitrogen or sulphur containing heterocyclic ring which is connected to the —$(CH_2)_y$— group through a ring carbon atom, y is 0 or 1, L is a group containing 1 or 2 carbon atoms, or is a single bond, $R_9$ and $R_{10}$, which may be the same or different, are each hydrogen, alkyl, phenyl or cycloalkyl, each of which optionally is substituted by phenyl, the phenyl groups in turn optionally being substituted by alkyl, or $R_9$ is as defined above and $R_{10}$ is —$OR_{11}$ or —$NR_{12}R_{13}$, wherein $R_{11}$, $R_{12}$ and $R_{13}$, which may be the same or different, are each hydrogen, cycloalkyl, alkanoyl, pyridyl, phenyl or alkyl optionally substituted by halogen or by =O, or $R_{10}$ is as defined above and $R_9$ forms part of a double bond with L, when L is a group containing 1 or 2 carbon atoms or $R_9$ and $R_{10}$, together with the nitrogen atom to which they are attached, form a 4 to 8 inclusive membered ring which optionally contains 0, 1 or 2 further hetero atoms, which ring carries substituents selected from the values of $R_1$ to $R_8$, or when L is a single bond and $R_9$ is as defined above then $R_8$ and —$NR_{10}$ may, together with the carbon atoms of the ring to which —$NR_{10}$ and $R_8$ are attached, form a 4 to 8 inclusive membered saturated or unsaturated ring which may contain 0, 1 or 2 further hetero atoms, which ring carries substituents $R_{16}$ to $R_{25}$, save that when —$NR_{10}$ forms part of a double bond with an adjacent carbon atom, $R_9$ has no significance, or when L is not a single bond the group —$LNR_9R_{10}$ forms a 5 or 6 membered nitrogen containing heterocyclic ring, which ring carries substituents $R_{26}$ to $R_{33}$, $R_1$ to $R_8$ and $R_{16}$ to $R_{33}$, which may be the same or different, are each hydrogen, halogen, phenoxy, alkyl, fluoroalkyl, alkanoyl, benzoyl, $RS(O)_n$—, —$NO_2$, —$NRR_{14}$, —$NHCOR$, —$COOH$ or an ester or amide thereof, or alkoxy optionally substituted by phenyl, and in addition, an adjacent pair of $R_1$, $R_2$, $R_3$, $R_4$, $R_5$, $R_6$, $R_7$ and $R_8$ may together form a chain —$(CH_2)_x$— or, together with the carbon atoms to which they are attached, form a 6 membered carbocyclic or nitrogen heterocyclic ring, n is 0, 1 or 2, x is 3, 4 or 5, X is S, O or $NR_{15}$, $R_{15}$ is hydrogen, —COR, —COOR or alkyl which latter is optionally substituted by —OCOR or by phenyl, R and $R_{14}$, which may be the same or different are each hydrogen, phenyl, or alkyl optionally substituted by phenyl, the phenyl groups in turn optionally being substituted by alkyl, provided that (i) at least one of $R_1$ to $R_7$ is other than hydrogen when y is 0, L is a single bond, X is NH, A represents a benzene ring and, (a) $R_9$ has no significance, and $R_8$ and —$NR_{10}$, together with the carbon atoms of the ring to which —$NR_{10}$ and $R_8$ are attached, form a 6 membered fully unsaturated, unsubstituted ring containing no further heteroatoms, or when (b) $R_8$, $R_9$ and $R_{10}$ are all hydrogen, (ii) when y is 1, L is not a single bond save when $R_8$ and —$NR_{10}$, together with the carbon atoms of the ring to which —$NR_{10}$ and $R_8$ are attached, form a 4 to 8 inclusive membered unsaturated ring which contains, 0, 1 or 2 further heteroatoms, which ring carries substituents $R_{16}$ to $R_{25}$, and pharmaceutically acceptable salts thereof.

We also provide the compounds of formula I, without proviso (i)(a), and pharmaceutically acceptable salts thereof, for use as pharmaceuticals, e.g. for use as cytoprotective agents, in the treatment or prophylaxis of inflammatory conditions, or in the prevention or inhibition of gastric acid secretion.

According to the invention we also provide a process for the production of a compound of formula I, or a pharmaceutically acceptable salt thereof, which comprises (a) selective oxidation of a corresponding compound of formula VI,

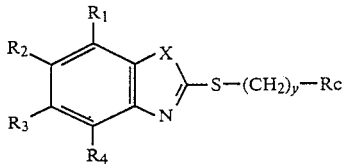

VI in which $R_1$, $R_2$, $R_3$, $R_4$, X, y and $R_c$ are as defined above, or (b) production of a compound of formula I carrying an —$NH_2$ group by selective reduction of a corresponding compound of formula I carrying an —$NO_2$ group, or (c) production of a compound of formula I in which X is —$NR_{15}$ and $R_{15}$ is as defined above save that it cannot be hydrogen, by reaction of a corresponding compound of formula I in which $R_{15}$ is hydrogen with a compound $R_{15}Z$ in which $R_{15}$ is as defined above, save that it cannot be hydrogen, and Z is a good leaving group, and where desired or necessary converting the resulting compound of formula I to a pharmaceutically acceptable salt thereof, or vice versa.

The oxidation of process (a) may be carried out in a solvent which is inert under the reaction conditions, e.g. ethyl acetate, dichloromethane, chloroform or a mixture thereof. The reaction is preferably carried out at less than room temperature, e.g. −20° to +10° C. Suitable oxidising agents for use in the reaction are hydrogen peroxide; peracids, e.g. m-chloroperbenzoic acid; or t-butylhydroperoxide in the presence of a suitable catalyst, e.g. vanadylacetylacetonate.

In process (b) the selective reduction may, for example, be carried out chemically under basic conditions, e.g. using hydrazine and Raney nickel, but is preferably carried out catalytically, e.g. using a $PtO_2$ catalyst and ethanol as the reaction medium.

In process (c) the good leaving group may be, for example, halogen (chlorine or iodine), and the reaction may be carried out in a solvent which is inert under the reaction conditions, e.g. dimethyl formamide, in the presence of a base, e.g. potassium carbonate and at a temperature of from about 15° to 30° C.

The compounds of formula VI may be made by conventional processes known per se, e.g. by reaction of a compound of formula VII,

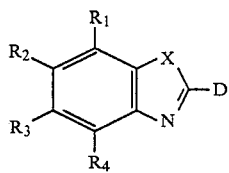

VII in which $R_1$, $R_2$, $R_3$, $R_4$ and X are as defined above, with a compound of formula VIII,

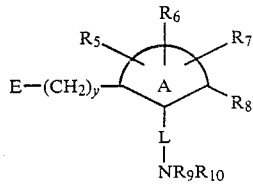

VIII in which $R_5$, $R_6$, $R_7$, $R_8$, $R_9$, $R_{10}$, L, y and A are as defined above, and
one of D and E is —SH and the other is a good leaving group, e.g. halogen (chlorine or bromine).

The reaction may be carried out in any suitable solvent, e.g. N,N-dimethyl formamide or N,N-dimethyl acetamide, at an optionally elevated temperature and may take place in the presence of a catalyst, e.g. Cu; or an acid acceptor, e.g. potassium carbonate.

The compounds of formulae VII and VIII are either known or may be made from known compounds using conventional techniques known per se.

The compounds of formula VI in which the group —$LNR_9R_{10}$ forms a pyridine ring may also be made by diazotisation of a compound of formula IX,

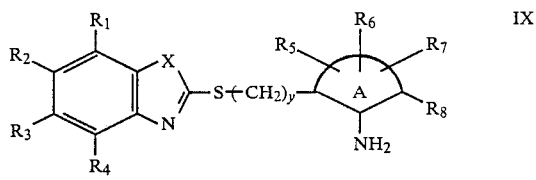

IX in which $R_1$ to $R_8$, X, A and y are as defined above, followed by reaction with pyridine.

The diazotisation may be carried out in any suitable solvent, e.g. water, in the presence of acid, e.g. hydrochloric acid, at a temperature in the range 0°–15° C., e.g. below 5° C., and with an alkali metal nitrite, e.g. sodium nitrite. Pyridine may be mixed with the diazonium salt and the subsequent reaction carried out at a temperature in the range 50° to 100° C., e.g. at about 80° C.

The compounds of formula IX are either known or may be made by conventional processes known per se, e.g. by processes analogous to those described above for the preparation of compounds of formula VI.

The compounds of formula I, and the intermediates therefor, may be isolated from their reaction mixtures using conventional techniques.

Pharmaceutically acceptable salts of the compounds of formula I include salts with suitable organic or inorganic acids, e.g. with a hydrohalic, sulphuric, alkanesulphonic, tartaric or citric acid. We also provide, when the compound of formula I carries a —COOH, or other acidic group, salts with suitable organic or inorganic bases, e.g. ammonium, alkali metal, alkaline earth metal, alkylamino, etc. salts. The benzimidazole nucleus itself is acidic and can form salts with appropriate bases as above.

The compounds of formula I, and pharmaceutically acceptable salts thereof, are useful because they possess pharmacological activity in animals; in particular they are useful because they have cytoprotective properties, are useful in the treatment or prophylaxis of inflammatory situations and/or prevent or inhibit gastric acid secretion, e.g. in the test set out in Am.J.Physiol., 1982, 243(6), G505–510. The compounds of formula I are also useful as intermediates in the synthesis of other chemicals.

The new compounds are thus indicated for use in the prevention or inhibition of gastric acid secretion, and/or conditions normally involving excess gastric acid secretion, e.g. peptic, duodenal, gastric, recurrent or stormal ulceration, dyspepsia, duodenitis, Zollinger-Ellison syndrome, reflux oesophagitis and the management of haemorrhage, e.g. from erosion of ulcers in the upper gastrointestinal tract, especially when a major blood vessel is not involved. The compounds may also be used to treat gastritis or dyspepsia associated with administration of non-steroidal anti-inflammatory drugs, in the prophylaxis of gastrointestinal haemorrhage from stress ulceration in seriously ill or burned patients, in the prophylaxis of recurrent haemorrhage in patients with bleeding peptic ulcers, before general anaesthesia in patients at risk of acid aspiration syndrome (Mendelson's syndrome) and to reduce the chance of haemorrhage in patients with leukaemia, graft versus host disease or with severe hepatic failure. The above conditions may be treated whether or not they are associated with excess gastric acid secretion.

The new compounds are also indicated for use as cytoprotective agents, especially for the gastrointestinal tract, and can be utilized for the treatment or prevention of a non-gastric-acid-induced, non-traumatically-induced, non-neoplastic gastrointestinal inflammatory disease for example, Crohn's disease, inflammatory bowel disease, infectious enteritis, colitis, ulcerative colitis, pseudomembranous colitis, diverticulitis, and allergenic and radiological inflammatory diseases.

The compounds are also indicated for use in the treatment or prophylaxis of inflammatory conditions in mammals, including man, especially those involving lysozymal enzymes. Conditions that may be specifically mentioned are: rheumatoid arthritis, gout, eczema, polyserositis and allergic alveolitis.

Patterns of therapeutic use which may be mentioned are:
(a) a high dose initially, for say 2-4 weeks, followed by lower-dose maintenance therapy after the condition has improved, e.g. the ulcer has healed,
(b) as in (a) above, but the maintenance therapy including another cytoprotective agent, e.g. a $PGE_2$ derivative,
(c) combination therapy, using a low dose of the compound of the invention in association with a low, well-tolerated dose of another cytoprotectant and/or antacid,
(d) intermittent dosing, e.g. every second day, may be appropriate as maintenance therapy.

For the above mentioned uses the dosage administered will, of course, vary with the compound employed, the mode of administration and the treatment desired. However, in general, satisfactory results are obtained when the compounds are administered at a dosage of from $10^{-6}M$ to $10^{-4}M$ in the test set out in Am.J.Physiol, 1982, 243 (6), G505-G510. For man the indicated total daily dosage is in the range of from about 1 mg to 3,000 mg, preferably 5 to 500 mg, and more preferably from about 10 mg to 200 mg, which may be administered in divided doses from 1 to 6 times a day or in sustained release form. Thus unit dosage forms suitable for administration comprise from about 1.0 mg to 600 mg of the compound admixed with a solid or liquid pharmaceutically acceptable diluent, carrier or adjuvant.

The compounds of formula I, and pharmaceutically acceptable salts thereof, have the advantage that they are more readily absorbed, or are less irritant to the GI tract, or have less toxic side effects, or are more active, or are more stable to gastric acid when administered by ingestion than compounds of similar structure.

We prefer at least one of $R_1$ to $R_8$, $R_{16}$ to $R_{33}$ to be other than hydrogen.

When any of $R_1$ to $R_8$, $R_{16}$ to $R_{33}$ is halogen, it may be chlorine or fluorine.

When any of $R_1$ to $R_{33}$ or R, represent or contain a carbon containing group we prefer that group to contain up to and including 10, and preferably up to and including 6, carbon atoms.

Specific groups $R_9$ and $R_{10}$ which may be mentioned include hydrogen, methyl and phenyl.

When $R_9$ and $R_{10}$ together with the nitrogen atom to which they are attached form a ring, the ring may be saturated or unsaturated and may contain a further nitrogen, oxygen and/or sulphur atom. We prefer that ring to be a piperidino or morpholino ring. We prefer that ring to carry 0, 1, 2 or 3 substituents selected from the values of $R_1$ to $R_8$, other than hydrogen.

We prefer ring A to be aromatic. Examples of ring A which may be mentioned are thiophene, pyrazole and preferably pyrimidine, benzene or pyridine. We particularly prefer ring A to be a benzene ring.

The number of substituents $R_5$ to $R_7$, $R_{16}$ to $R_{25}$, $R_{26}$ to $R_{33}$ clearly cannot be more than the number of positions available for substitution on the ring.

When any of $R_1$ to $R_8$, $R_{16}$ to $R_{33}$ represent an ester we prefer it to be with a C 1 to C6 alcohol, e.g. to be an ethyl or methyl ester. When any of $R_1$ to $R_8$, $R_{16}$ to $R_{33}$ represent an amide they may be, for example, an unsubstituted or a mono- or di-alkyl C 1 to C6 substituted amide. When an adjacent pair of $R_1$ to $R_8$ together form a chain we prefer that chain to be —CH=CH—CH=CH— or —(CH$_2$)$_4$—.

Specific groups $R_1$ to $R_8$, $R_{16}$ to $R_{33}$ include hydrogen, methoxycarbonyl, phenylcarbonyl, methyl, ethyl, propyl, butyl, chloro, methoxy, ethoxy, propyloxy, —NHCOCH$_3$, benzoyl, benzyloxy, phenoxy, CF$_3$, —N(CH$_3$)$_2$, p-toluenesulphonyl and —NH$_2$, and/or an adjacent pair of $R_1$ to $R_8$ may together form a —CH=CH—CH=CH— chain.

We prefer $R_1$ to $R_8$, $R_{16}$ to $R_{33}$ to be selected from hydrogen, methoxy, methoxycarbonyl, propyloxy, methyl, —CF$_3$, chloro, —NO$_2$, —NH$_2$, —N(CH$_3$)$_2$ or to form a —CH=CH—CH=CH— chain.

We prefer y to be 0.

We prefer X to be S or —NR$_{15}$.

Specific groups $R_{15}$ are H, acetyl, —CO$_2$CH$_2$Ph, —CH$_2$Ph, —CH$_2$OCOt-butyl, —COOethyl and methyl.

We prefer $R_{15}$ to be H, methyl or —CO$_2$CH$_2$Ph.

When L represents a single bond, y is 0, A is a benzene ring, and $R_9$ and $R_{10}$ are each hydrogen or alkyl C 1 to C6, we prefer the benzene ring to carry in addition to the group —L—NR$_9$R$_{10}$ a substituent —NH$_2$ or —NRR$_{14}$. We particularly prefer the substituent —NH$_2$ or —NRR$_{14}$ to be positioned para to the —L—NR$_9$R$_{10}$ group. We prefer —NRR$_{14}$ to be —N(CH$_3$)$_2$.

When L is a single bond and $R_8$ and —NR$_{10}$, together with the carbon atoms of the ring to which $R_8$ and —NR$_{10}$ are attached, form a ring, we prefer that ring to be a nitrogen heterocyclic ring optionally containing an oxygen atom for example, we prefer that ring to be an imidazole, pyridine, pyrrole or piperidino ring, e.g. an N-methyl piperidino ring. We particularly prefer that ring to be a pyridine ring. We prefer the ring to be substituted by 1, 2 or 3 substituents $R_{16}$ to $R_{25}$ other than hydrogen.

When $R_8$ and $-NR_{10}$ form part of a pyridine ring, as described above, we prefer A to represent a benzene ring, and X to be $NR_{15}$.

When $R_8$ and $-NR_{10}$ form part of a pyridine ring as described above, we prefer that ring to have a substituent $R_{16}$ to $R_{25}$ other than hydrogen para to the nitrogen of the group $-NR_{10}$. We prefer that substituent to be an electron donating substituent, e.g. alkoxy, phenoxy, benzyloxy, amino or alkyl C 1 to C6. We particularly prefer the substituent para to the ring nitrogen atom to be alkoxy, e.g. methoxy.

When L is a group containing 1 or 2 carbon atoms it may be for example, $-CH_2CH_2-$, $-CH=$, $-CH_2CH=$ or preferably $-CH_2-$.

When the group $-LNR_9R_{10}$ forms a 5 or 6 membered nitrogen containing heterocyclic ring, that ring may be saturated or unsaturated.

Specific groups $-LNR_9R_{10}$ which may be mentioned include

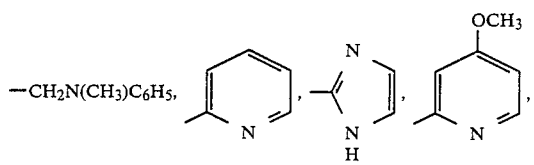

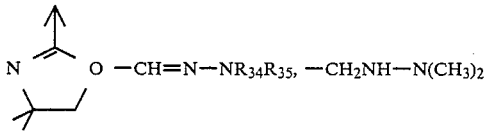

and $-CH=N-OR_{36}$, in which $R_{34}$, $R_{35}$ and $R_{36}$, which may be the same or different, are each hydrogen, alkyl C 1 to C6 or phenyl.

We prefer $-LNR_9R_{10}$ to form a 2-pyridyl group.

When the group $-LNR_9R_{10}$ forms a 2-pyridyl group we prefer that group to be substituted by 1, 2 or 3 substituents $R_{26}$ to $R_{33}$ other than hydrogen. We prefer that group to have a substituent para to the nitrogen atom of the group $-NR_9R_{10}$. We prefer that substituent to be an electron donating substituent, e.g. alkoxy C 1 to C6, amino or alkyl C 1 to C6. We particularly prefer that substituent to be methoxy.

When the group $-LNR_9R_{10}$ forms a 2-pyridyl group, we prefer A to represent a benzene ring, and X to be $NR_{15}$.

Specific groups of compounds of formula I include (a)

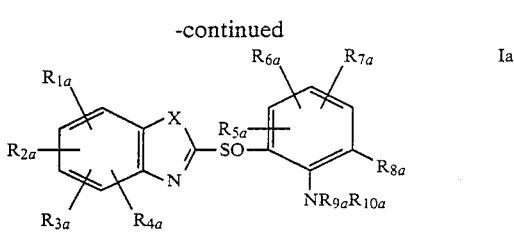

in which $R_{1a}$, $R_{2a}$, $R_{3a}$, $R_{4a}$, $R_{5a}$, $R_{6a}$, $R_{7a}$ and $R_{8a}$, which may be the same or different, are each hydrogen, halogen, alkoxy, alkyl, fluoroalkyl, alkanoyl, $RS(O)_n-$, $-NO_2$, $-N(R)_2$, $-NHCOR$, or $-COOH$ or an ester or amide thereof, or an adjacent pair of $R_{1a}$, $R_{2a}$, $R_{3a}$, $R_{4a}$, $R_{5a}$, $R_{6a}$, $R_{7a}$ and $R_{8a}$ may in addition to the values given above, together form a chain $-(CH_2)_x-$ or, together with the carbon atoms to which they are attached, form a 6 membered unsaturated carbocylic or nitrogen heterocyclic ring, x, n, X and R are as defined above, $R_{9a}$ and $R_{10a}$, which may be the same or different, are each hydrogen, alkyl, phenyl or cycloalkyl each of which may optionally be substituted by phenyl, the phenyl group in turn optionally being substituted by alkyl, or one of $R_{9a}$ and $R_{10a}$ may be as defined above and the other may be $-OR_{11}$ or $-NR_{12}R_{13}$, or $R_{9a}$ and $R_{10a}$, together with the nitrogen atom to which they are attached may form a saturated or unsaturated 4 to 8 inclusive membered ring which may contain 0, 1 or 2 further hetero atoms, which ring may carry one or more substituents $R_{1a}$, and $R_{11}$, $R_{12}$ and $R_{13}$, are as defined above, or $R_{9a}$ is as defined above save that it cannot form a ring with $R_{10a}$, and $R_{8a}$ and $R_{10a}$, together with the nitrogen atom and the carbon atoms of the ring to which the nitrogen atom and $R_{8a}$ are attached, form a saturated 4 to 8 inclusive membered ring which may contain 0, 1, or 2 further hetero atoms, which ring may carry one or more substituents $R_{1a}$, with the proviso i(a) above, (b)

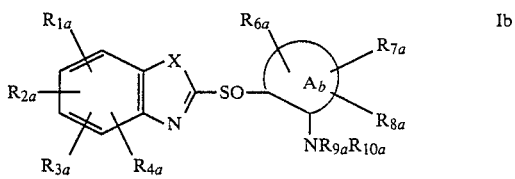

in which $R_{1a}$ to $R_{4a}$, $R_{6a}$ to $R_{10a}$ and X are as defined above, and $A_b$ represents a 5 or 6 membered nitrogen or sulphur containing heterocyclic ring which is connected to the rest of the molecule through a ring carbon atom, (c)

-continued

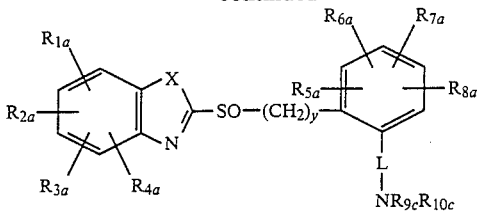
Ic in which $R_{1a}$ to $R_{8a}$, y and X are as defined above, $R_{9c}$ and $R_{10c}$, which may be the same or different, are each hydrogen, alkyl, phenyl or cycloalkyl each of which may optionally be substituted by phenyl, the phenyl groups in turn optionally being substituted by alkyl, or one of $R_{9c}$ and $R_{10c}$ is as defined above and the other is $-OR_{11}$ or $-NR_{12}R_{13}$, or one of $R_{9c}$ and $R_{10c}$ is as defined above and the other forms a part of a double bond with $L_c$, or $R_{9c}$ and $R_{10c}$, together with the nitrogen atom to which they are attached may form a saturated or unsaturated 4 to 8 inclusive membered ring which may contain 0, 1 or 2 further hetero atoms, which ring may carry one or more substituents $R_{1a}$, and $R_{11}$, $R_{12}$ and $R_{13}$, are as defined above, $L_c$ is a group containing 1 or 2 carbon atoms inclusive, or the group $-L_c-NR_{9c}R_{10c}$ may form a 5 or 6 membered nitrogen containing heterocyclic ring, (d)

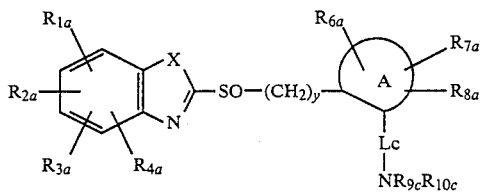

in which $R_{1a}$ to $R_{4a}$, $R_{6a}$ to $R_{8a}$, $R_{9c}$, $R_{10c}$, $L_c$, $A_b$, X and y are as described above.

(e)

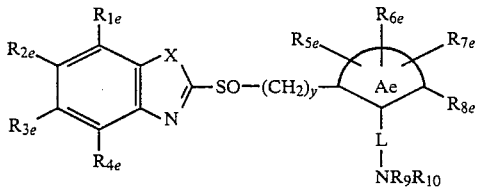
I in which $A_e$ represents a benzene ring, or a 5 or 6 membered nitrogen or sulphur containing heterocyclic ring which is connected to the rest of the molecule through a ring carbon atom, y, L, $R_9$ and $R_{10}$ are as defined above, $R_{1e}$ to $R_{8e}$, which may be the same or different, are each hydrogen, halogen, phenoxy, alkyl, fluoroalkyl, alkanoyl, $RS(O)_n-$, $-NO_2$, $-NRR_{14}$, $-NHCOR$, $-COOH$ or an ester or amide thereof, or alkoxy optionally substituted by phenyl, and in addition, an adjacent pair of $R_{1e}$, $R_{2e}$, $R_{3e}$, $R_{4e}$, $R_{5e}$, $R_{6e}$, $R_{7e}$ and $R_{8e}$ may together form a chain $-(CH_2)_x-$ or, together with the carbon atoms to which they are attached, form a 6 membered carbocylic or nitrogen heterocyclic ring, R, $R_{14}$, n and x are as defined above, X is S, O or $NR_{15}$, $R_{15}$ is hydrogen, $-COR$, $-COOR$ or alkyl which latter is substituted by $-COR$, with the provisos i(a), (b) and (ii) above.

Certain of the compounds of formula VI are novel and the invention also provides these novel compounds.

According to our invention we also provide a pharmaceutical composition comprising (preferably a minor proportion of) a compound of formula I, or a pharmaceutically acceptable salt thereof, as active ingredient, in admixture with a pharmaceutically acceptable adjuvant, diluent or carrier. Examples of suitable adjuvants, diluents or carriers are:- for tablets and dragees; lactose, starch, talc or stearic acid; for capsules, tartaric acid or lactose; for suppositories, natural or hardened oils or wax; and for injections (i.m. or i.v.) or enemas water, surfactants and preservatives. The compounds may also be administered transdermally, e.g. in an ointment base. The compound of formula I, or the pharmaceutically acceptable salt thereof, preferably has a mass median diameter of from 0.01 to 10 microns. The compound of such particle size may be made by grinding or milling followed if necessary by particle size classification using, for example, a sieve. The compositions may also contain suitable preserving, stabilising, and wetting agents, solubilizers, sweetening and colouring agents and flavourings. The compositions may, if desired, be formulated in sustained release form.

The compounds may, if desired, be co-administered, with (e.g. as a mixture with) an antacid buffer.

We prefer compositions which are designed to be taken by ingestion or rectally and to release their contents in the intestine. We particularly prefer compositions which will pass through the acidic parts of the gastrointestinal tract unaffected, e.g. enteric coated formulations.

The compounds of formula I are optically active and may be resolved into their optical isomers using conventional techniques known per se. The invention therefore provides the compounds as their optical isomers, or as mixtures, e.g. racemic mixtures, thereof.

The invention is illustrated, but in no way limited by the following Examples in which temperatures are in degrees centigrade.

EXAMPLE 1

2-(1H-Benzimidazol-2yl sulphinyl)-N,N-dimethyl benzenamine (a) 2-(N,N-Dimethylamino)-phenyldisulphide 2-Aminophenyldisulphide (10 g) was suspended in water (42 ml) and sodium bicarbonate (28 g) added. The mixture was stirred vigorously with ice bath cooling while dimethylsulphate (28.3 ml) was added dropwise over 10 minutes. The mixture was heated to 60° and stirred overnight. The cooled mixture was made strongly basic with sodium hydroxide solution and stirred for two hours. The mixture was diluted with water and extracted with ethyl acetate. The ethyl acetate was washed with water and brine, and then dried and evaporated. The resulting brown oil was triturated with 40°-60° petroleum ether which produced fine crystals. The crystals were filtered and dried affording 7.11 g of the desired product. NMR (CDCl$_3$) delta 7.50 (m 2H) 7.10 (m 6H) 2.81 (s 12H).

(b) 2-(1H-Benzimidazol-2-yl thio)-N,N-dimethyl benzenamine

To a stirred solution of the product of step (a) (2.0 g) in dry tetrahydrofuran (100 ml) was added a solution of lithium aluminium hydride (20 ml of 1M in ether) dropwise. After 1 hour water was added dropwise. When the vigorous effervescence had ceased the mixture was poured onto water and made acidic with dilute hydrochloric acid. After shaking, the solution was basified with sodium bicarbonate and extracted with ethyl acetate. The ethyl acetate was washed with water and brine, and then dried and evaporated to leave a clear oil (1.52 g). The oil was stirred under nitrogen with 2-chlorobenzimidazole (1.4 g) in dry degassed dimethylformamide (50 ml) at 80° for 1 hour. The cooled mixture was poured into an aqueous sodium bicarbonate solution and the product extracted with ethyl acetate. The ethyl acetate was washed with brine, and then dried and evaporated. The residue was crystallised from ethyl acetate to afford the sub-title compound as prisms 670 mg, mp 148°–9°.

(c) 2-(1H-Benzimidazol-2-yl sulphinyl)-N,N-dimethyl benzenamine

The product of step (b) (4.1 g) was dissolved in ethyl acetate (130 ml) and the stirred solution cooled to −10°. An ice cold solution of m-chloroperbenzoic acid (2.77 g of 95%) in ethyl acetate (20 ml) was added. The resulting solution was stirred for 40 minutes, and then washed with sodium bicarbonate solution, water and brine, dried and evaporated. The residue was purified by flash chromatography to produce a colourless foam. The foam was subjected to high vacuum which afforded 3.18 g of the title compound.
NMR (CDCl$_3$) delta 11.86 (broad s 1H) 7.77 (d.o.d.), 7.74 (broad 2H), 7.43 (m 2H), 7.25 (m 2H), 7.19 (d.o.d. 1H), 7.13 (m 1H), 2.90 (s 6H).

EXAMPLE 2

By the method described in Example 1, and using the appropriate starting materials, may be prepared the following compounds:
(a)
  (i) 2-(1H-Benzimidazol-2-yl thio)-N,N-dimethyl-4-methyloxy benzenamine mp 150°–153°.
  (ii) 2-(1H-Benzimidazol-2-yl sulphinyl)-N,N-dimethyl-4-methyloxy benzenamine mp 178°–9°.
(b)
  (i) 2-(5-Chloro-1H-benzimidazol-2-yl thio)-N,N-dimethyl benzenamine mp 152°.
  (ii) 2-(5-Chloro-1H-benzimidazol-2-yl sulphinyl)-N,N-dimethyl benzenamine mp 132°–3° (dec).
(c)
  (i) 2-(5-Nitro-1H-benzimidazol-2-yl thio)-N,N-dimethyl benzenamine mp 78°–80°.
  (ii) 2-(5-Nitro-1H-benzimidazol-2-yl sulphinyl)-N,N-dimethyl benzenamine mp 180°–181°.
(d)
  (i) 2-(5-Chloro-1H-benzimidazol-2-yl thio)-4-methoxy-N,N-dimethyl benzenamine mp 138°–9°.
  (ii) 2-(5-Chloro-1H-benzimidazol-2-yl sulphinyl)-4-methoxy-N,N-dimethyl benzenamine NMR (CDCl$_3$) delta:11.6 (broad, 1H), 7.3 (m,5H), 6.95 (dod,1H), 3.68 (s,3H), 2.72 (s,6H).
(e)
  (i) 2-(1H-Benzimidazol-2-yl thio)-4-(1-methylethoxy)-N,N-dimethyl benzenamine mp 172°–3°.
  (ii) 2-(1H-Benzimidazol-2-yl sulphinyl-4-(1-methylethoxy)-N,N-dimethyl benzenamine mp 172°–3°.
(f)
  (i) 2-(5,6-Dichloro-1H-benzimidazol-2-yl thio)-4-methoxy-N,N-dimethyl benzenamine mp 207°–8°.
  (ii) 2-(5,6-Dichloro-1H-benzimidazol-2-yl sulphinyl)-4-methoxy-N,N-dimethyl benzenamine mp 164°–5°.
(g)
  (i) Methyl 2-(2-dimethylamino-5-methoxyphenyl thio)-1H-benzimidazole-5-carboxylate m/z 357, 190 (base peak), 171, 169.
  (ii) Methyl 2-(2-dimethylamino-5-methoxyphenyl sulphinyl)-1H-benzimidazole-5-carboxylate C$_{18}$H$_{19}$O$_4$SN$_3$
Found C, 57.49; H, 5.11; N, 10.88; S, 8.59; H$_2$O, 0.2% (Karl-Fischer) 0.2% water requires: C, 57.84; H, 5.1; N, 11.23; S, 8.55%

EXAMPLE 3

2-(5-Chloro-1H-benzimidazol-2-yl sulphinyl)benzenamine (a) 2-(5-Chloro-1H-benzimidazol-2-yl thio)benzenamine 2-(5-Chloro-1H-benzimidazol-2-yl thio)nitrobenzene (0.3 g) was dissolved in dry ethanol (100 ml) with warming and the solution was hydrogenated in the presence of 10% Pd/C at 3 atmospheres pressure and 50° for 2.75 hours. The heating and stirring were stopped and the mixture was left standing under an H$_2$ atmosphere overnight. The mixture was then filtered through a filter aid and evaporated under reduced pressure, and dried under vacuum at 50° to leave the sub-title compound as a pale greenish glassy solid (0.23 g), mp 155°–156°.

(b) 2-(5-Chloro-1H-benzimidazol-2-yl sulphinyl) benzenamine

The product of step (a) (5.1 g) in dichloromethane (150 ml) stirring in an ice bath (approx. 5°) was treated dropwise with 95% m-chloroperbenzoic acid (3.51 g) in dichloromethane (80 ml). The mixture was stirred in the ice bath for 2 hours and then poured onto saturated aqueous sodium bicarbonate solution. The organic layer was separated, washed, dried and evaporated under reduced pressure to leave 4.61 g of creamish/grey glassy solid. This was taken up in a small volume of CH$_2$Cl$_2$/ethyl acetate 9/1 and the insoluble material filtered off, washed with petroleum ether (30°–40°) and dried under vacuum at 50°. to give 2.63 g of the desired product, mp 176°–178°.

EXAMPLE 4

By the method of Example 3, and using appropriate starting materials, may be prepared the following compounds:
(a)
  (i) 2-(5-Methoxy-1H-benzimidazol-2-yl thio) benzenamine mp 61°–64°.
  (ii) 2-(5-Methoxy-1H-benzimidazol-2-yl sulphinyl) benzenamine mp 73°–75°.
(b)
  (i) 2-(5,6-Dimethoxy-1H-benzimidazol-2-yl thio) benzenamine mp 79°–80°.
  (ii) 2-(5,6-Dimethoxy-1H-benzimidazol-2-yl sulphinyl)-benzenamine C$_{15}$H$_{15}$O$_3$SN$_3$
Found: C, 56.08; H, 4.89; N, 12.66; S, 9.62%
Required: C, 56.78; H, 4.73; N, 13.25; S, 10.09%

EXAMPLE 5

N-[2-(1H-Benzimidazol-2-yl sulphinyl)phenylmethyl]-N-methyl-benzenamine (a) N,N'-Dimethyl-N,N'-(2,2'-diphenyl methyldithio)-bis-benzenamine Di-(2-chloromethylphenyl)disulphide (7.4 g) and N-methyl benzenamine (11.77 g) were heated at 100° in dry dimethylformamide (200 ml) for 72 hours. The reaction mixture was poured into water and extracted into ether. The organic phase was washed with water, dried and evaporated. The residue was chromatographed (SiO₂/3:1 petroleum ether-ethyl acetate) to afford the sub-title compound (4.2 g). Mass spectrum: M+ 456. Base Peak (BP) 228.

(b) N-[2-(1H-Benzimidazol-2-yl thio)phenylmethyl]-N-methyl-benzenamine

The product of step (a) was converted into the sub-title compound by the method of Example 1(b), mp 168°–9°.

(c) N-[2-(1H-Benzimidazol-2-yl sulphinyl)phenylmethyl]-N-methyl-benzenamine

The product of step (b) was converted into the title compound by the method of Example 1 (c), mp 164°–6°.

EXAMPLE 6

2-(1-Methyl-1H-benzimidazol-2-yl sulphinyl)benzenamine 2-(1H-Benzimidazol-2-yl sulphinyl)benzenamine (850 mg, 3.31 mmole) in dimethylformamide (16 ml) and methyl iodide (515 mg, 3.63 mmole) were stirred at room temperature for 6 hours in a stoppered flask in the presence of potassium carbonate (1.66 g, 12 mmole). The mixture was poured into water and extracted with ethyl acetate (3×). The combined extracts were washed with water (3×), dried (anhydrous sodium sulphate) and evaporated to give a pale grey solid which was triturated with ether to give the title compound as an off-white solid (0.78 g; 87%), mp 146°–8° (dec).

EXAMPLE 7

By the method of Example 6, and using the appropriate starting materials, were made the following compounds:
(a)
(i) 2-(1-Methyl-1H-benzimidazol-2-yl sulphinyl)-N,N-dimethyl benzenamine mp 143°–4°.
(ii) 2-(5,6-Dichloro-1-methyl-1H-benzimidazol-2-yl sulphinyl)-4-methoxy-N,N-dimethyl benzenamine mp 132°–3° containing 2.35% water (Karl-Fischer analysis).

EXAMPLE 8

2-(5-Amino-1H-benzimidazol-2-yl sulphinyl)-N,N-dimethyl benzenamine 2-(5-Nitro-1H-benzimidazol-2-yl sulphinyl)-N,N-dimethylbenzenamine (3 g) was suspended in ethanol (300 ml), and hydrogenated at 1 atmosphere at room temperature, using platinum oxide as catalyst, for 3 days.

The catalyst was filtered off and solvent evaporated to give a yellow solid.

Purification by flash chromatography (silica, ethyl acetate: CH₂Cl₂; 2:1) gave the title compound, 1.01 g (37%), mp 178°.

EXAMPLE 9

2-(1H-Benzimidazol-2-yl sulphinyl)-N,N,N',N'-tetramethyl-1,4-benzenediamine (a) N,N,N',N'-tetramethyl-2,5-diaminophenyldisulphide 2-Amino-5-N,N-dimethylaminophenylthiosulphonic acid (22.6 g) was stirred with sodium bicarbonate (46 g) and water (70 ml) until effervescence had ceased. Dimethyl sulphate (43 ml) was added and the mixture heated at 60° for 5 hrs. To the cooled mixture 880 ammonia (10 ml) was added and the mixture stirred for 30 mins. The mixture was concentrated in vacuo and treated with a solution of diazobicylco[2.2.2.]octane (31 g) in ethanol (100 ml) and the resulting mixture heated under reflux for 2 hrs. The solvent was removed in vacuo and the residue treated with conc. hydrochloric acid (60 ml). The mixture was heated at 90° for 45 mins. The cooled mixture was poured onto sodium bicarbonate (100 g) and after addition of water (100 ml) was extracted with ethyl acetate. The ethyl acetate was washed with water and brine and then dried and evaporated. The residue was flash chromatographed to produce the desired compound as an orange oil (3.1 g) NMR (CDCl₃) delta 7.03 (1H)d, 6.95 (1H)d, 6.50 (1H)d.o.d., 2.78 (6H)s, 2.73 (6H)s.

(b) 2-(1H-Benzimidazol-2-yl thio)-N,N,N',N'-tetramethyl-1,4-benzenediamine

N,N,N',N'-tetramethyl-2,5-diaminophenyldisulphide (1.5 g) was dissolved in dry tetrahydrofuran (70 ml) and treated with an ethereal solution of lithium aluminium hydride (5.8 ml of 1M) dropwise over 20 mins. The solution was stirred for a further 40 mins. Water (100 ml) was added, dropwise initially until all vigorous effervescence had ceased, then more rapidly. The mixture was poured onto dilute hydrochloric acid and after mixing the solution was basified with sodium bicarbonate solution and extracted with ethyl acetate. The ethyl acetate was washed with brine, and then dried and evaporated to leave a clear oil 1.2 g. The oil was taken up in dry degassed dimethylformamide (50 ml) and a solution of 2-chlorobenzimidazole (930 mg) in dry degassed dimethylformamide (50 ml) was added. The mixture was stirred under nitrogen and heated to 80° for 2 hrs. The cooled mixture was poured onto water (200 ml) and basified with sodium bicarbonate solution. The precipitate was collected, washed well with water and then dried to afford the desired compound as a colourless solid (1.61 g) NMR (CDCl₃) delta 7.4 (broad 2H), 7.18 (2H)m, 7.14 (1H)d, 7.00 (1H)d, 6.71 (1H)d.o.d., 2.90 (6H)s, 2.86 (6H)s.

(c) 2-(1H-Benzimidazol-2-yl sulphinyl)-N,N,N',N'-tetramethyl-1,4-benzenediamine

The product of step (b) above (1.5 g) was dissolved in ethyl acetate (120 ml) and cooled to −10°. A solution of m-chloroperbenzoic acid (980 mg of 85%) in ethyl acetate (30 ml) was added in one portion and the mixture stirred for 1 hr. The mixture was filtered and the residue taken up in dichloromethane. The dichloromethane was washed with sodium bicarbonate solution, sodium metabisulphite solution, water and brine and then dried and evaporated. Flash chromatography afforded the title compound as an off white solid (857 mg) mp 213°–215° NMR (CDCl$_3$) delta 7.7 (broad), 7.4 (2H)broad, 7.20 (2H)m, 7.12 (2H)m, 6.69 (1H)d.o.d., 2.79 (6H) 2.60 (6H)s.

EXAMPLE 10

2-(4-Methoxyquinolin-8-yl sulphinyl)-1H-benzimidazole (a) 8-(1H-Benzimidazol-2-yl thio)-1,4-dihydro-quinolin-4-one 8,8'-Dithio bis (4-methoxyquinoline) (2.5 g) was suspended in dry tetrahydrofuran (100 ml) at room temperature under nitrogen and treated with lithium aluminium hydride in ethereal solution (15 mmole). After 2 hours water was added dropwise followed by dilute HCl and after 10 minutes the mixture was basified with NaHCO$_3$ solution. This suspension was extracted into ethyl acetate, which was washed with brine, then dried and evaporated in vacuo. The residue was dissolved in dry degassed dimethylformamide (40 ml) containing 2-chlorobenzimidazole (2.3 g) and heated at 80° for 18 hours. The solution was poured into water (600 ml) and the precipitate collected and washed with water. Trituration with boiling CH$_2$Cl$_2$ afforded the sub-title product as a yellow powder 1.2 g, mp greater than 240°.

(b) 2-(4-Methoxyquinolin-8-yl thio)-1H-benzimidazole

The product of step (a) above (2.1 g) was reacted with POCl$_3$ (50 ml) at gentle reflux for 1 hour, then cooled, and cautiously poured onto ice (500 ml), then neutralised with ammonia. The precipitate was collected and dried, then a solution of sodium (483 mg) in dry methanol (25 ml) was added and the whole was refluxed for 36 hours. The mixture was cooled and treated with ammonium chloride, then evaporated in vacuo. The solid was extracted into ethyl acetate and the product was isolated by column chromatography (SiO$_2$/2:1 ethyl acetate/petroleum ether) to afford the sub-title compound 430 mg, mp 218°–9°.

(c) 2-(4-Methoxyquinolin-8-yl sulphinyl)-1H-benzimidazole

The product of step (b) above (390 mg) in ethyl acetate (20 ml) was cooled to −5° and treated with m-chloroperbenzoic acid (273 mg of 85% pure material). The temperature was allowed to rinse to ambient. The reaction mixture was then diluted with ethyl acetate and methylene chloride, and then washed with sodium bisulphite solution, sodium bicarbonate solution and brine. The solution was dried and evaporated. Column chromatography (SiO$_2$/ethyl acetate) gave the title compound 140 mg, mp 178°–9° (d).

EXAMPLE 11

2-(4-Methoxyquinolin-8-yl methylsulphinyl)-1H-benzimidazole (a) 8-Bromomethyl-4-methoxyquinoline 4-Methoxy-8-methylquinoline (346 mg, 2 mmole), N-bromosuccinimide (365 mg, 2.05 mmole) and benzoyl peroxide (10 mg) in CCl$_4$ (8 ml) were heated under reflux for 2.5 hours. The mixture was cooled and the succinimide was filtered off. The filtrate was washed with dilute aqueous NaHCO$_3$ (1×) and water (1×), dried (Na$_2$SO$_4$) and evaporated to yield the sub-title compound as a pale yellow solid which was recrystallised from petroleum ether-cyclohexane to give colourless needles.
Yield 195 mg (38.6%).
MW 251/3 (207), 172 (base peak), (157), (142), (129), (115), (102), (91), (76), (63), (51), (39).

(b) 2-(4-Methoxyquinolin-8-yl methylthio)-1H-benzimidazole

The product of step (a) above and 2-mercapto benzimidazole (3.0 g, 20 mmole) were stirred at room temperature in dry dimethylformamide (75 ml) with K$_2$CO$_3$ (5.5 g, 40 mmole) for 4 hours. The mixture was poured into water and extracted with CHCl$_3$ (3×). The combined extracts were washed with water (3×), dried (Na$_2$SO$_4$) and evaporated to yield a cream solid which was recrystallised from ethyl acetate and then dried in vacuo at room temperature, mp 189°–192°.

(c) 2-(4-Methoxyquinolin-8-yl methylsulphinyl)-1H-benzimidazole

The product of step (b) above was converted by a method analogous to that of Example 3 (b) to the title compound, mp 214° (d)).

EXAMPLE 12

By the method of Example 11, and with the appropriate starting materials, was made the following compound:
(a)
  (i) 2-(Quinolin-8-yl methylthio)-1H-benzimidazole mp 165°–6°.
  (ii) 2-(Quinolin-8-yl methylsulphinyl)-1H-benzimidazole mp 207°–8°.

EXAMPLE 13

2-[2-(2-Pyridyl)-phenyl sulphinyl]-1H-benzimidazole (a) 2-[2-(2-Pyridyl)-phenyl thio]-1H-benzimidazole 2-(1H-Benzimidazol-2-yl thio)benzenamine (8.5 g) in dilute hydrochloric acid (680 ml) was cooled (0° to −5°) with stirring and sodium nitrite (2.68 g) in water (85 ml) was added dropwise, keeping the temperature below 0°. The resulting diazonium salt solution was stirred at 0° for 0.5 hours, then added portionwise to pyridine (800 ml) with stirring at 80° for 1 hour. The pyridine was distilled off, and replaced with 880 ammonia which was in turn distilled off. The residue was treated with water and extracted into dichloromethane, washed, dried, evaporated under reduced pressure and purified by flash column chromatography using dichloromethane:ethyl acetate, 9:2 as eluant to give 3.07 g of the sub-title product.
Elemental Analysis:
Found: C,70.48, H,4.52, N,13.48, S,9.93, KF1.7%
  C$_{18}$H$_{13}$N$_3$S 0.25H$_2$O
Required: C,70.20, H,4.39, N,13.66, S,10.43, KF,1.4%

(b) 2-[2-(2-Pyridyl)-phenyl sulphinyl]-1H-benzimidazole

The product of step (a) above (2.0 g) in dichloromethane (100 ml) was treated dropwise, stirring in an ice bath, with 95% m-chloroperbenzoic acid (1.31 g) in dichloromethane (50 ml) for 50 minutes. The reaction mixture was then poured onto a saturated aqueous sodium bicarbonate solution, extracted into dichloromethane, washed, dried and evaporated to leave a creamish solid. Trituration with petroleum ether (30° to 40°) and filtration give the title product as a cream solid, 1.89 g. M/S m/e 319 (M+, 45%), 186 (100%).

EXAMPLE 14

By the method of Example 13, and using the appropriate starting materials, were made the following compounds:

(a)
- (i) 5-Chloro-2-(2-(2-pyridyl)-phenyl thio)-1H-benzimidazole M.S. m/e 337 (M+, 25%), 186 (100%).
- (ii) 5-Chloro-2-(2-(2-pyridyl)-phenyl sulphinyl)-1H-benzimidazole M.S. m/e 354/6 (M++1) FAB m.s.

(b)
- (i) 2-[2-(2-Pyridyl)-phenyl thio]-benzothiazole m/e 320 Base Peak 186.
- (ii) 2-[2-(2-Pyridyl)-phenyl sulphinyl]-benzothiazole m/e Mwt + Base Peak 337 (M+1).

(c)
- (i) Methyl 2-(2-(2-pyridyl)-phenyl thio)-1H-benzimidazole-5-carboxylate m/z (FAB) 361 M+.
- (ii) Methyl 2-(2-(2-pyridyl)-phenyl sulphinyl)-1H-benzimidazole-5-carboxylate m/z (FAB) 378 (M++1).

(d)
- (i) 4-Trifluoromethyl-2-[2-(2-pyridyl)-phenyl thio]-1H-benzimidazole mp 169°-171°.
- (ii) 4-Trifluoromethyl-2-[2-(2-pyridyl)-phenyl sulphinyl]-1H-benzimidazole mp 224°-5°.

(e)
- (i) 2-[2-(2-Pyridyl)-phenyl thio]-naphtho[2,3-d]imidazole m/z 353 (M+).
- (ii) 2-[2-(2-Pyridyl)-phenyl sulphinyl]-naphtho[2,3-d]imidazole m/z (FAB) 370 (M+1).

(f)
- (i) 2-[5-Chloro-2-(2-(2-pyridyl)-phenyl thio]-5-methoxy-1H-benzimidazole m/z 367/369 (M+).
- (ii) 2-[5-Chloro-2-(2-(2-pyridyl)-phenyl sulphinyl]-5-methoxy-1H-benzimidazole mp 113° (d).

(g)
- (i) 5,6-Dimethyl-2-[2-(2-pyridyl)-phenyl thio]-1H-benzimidazole mp 196°-8°.
- (ii) 5,6-Dimethyl-2-[2-(2-pyridyl)-phenyl sulphinyl]-1H-benzimidazole mp 219°-221°.

(h)
- (i) 5-Methyl-2-[2-(2-pyridyl)-phenyl thio]-1H-benzimidazole m/z 317 (M+).
- (ii) 5-Methyl-2-[2-(2-pyridyl)-phenyl sulphinyl]-1H-benzimidazole mp 110°.

(i)
- (i) 5-(4-Methylphenylsulphonyl)-2-[2-(2-pyridyl)-phenyl thio]-1H-benzimidazole MW (fast atom bombardment) 426 (M++1).
- (ii) 5-(4-Methylphenylsulphonyl)-2-[2-(2-pyridyl)-phenyl sulphinyl]-1H-benzimidazole MW (fast atom bombardment) 422 (M++1).

(j)
- (i) N-[4-(4,7-dimethoxy-1H-benzimidazol-2-yl thio)-3-(2-pyridyl)-phenyl]acetamide
NMR delta (DMSO d6) 2.05 (3Hs), 3.82 (6Hs), 6.53 (1Hd), 6.62 (1Hd), 7.19 (1Hd), 7.42 (1Hm), 7.49 (1H dod), 7.7 (1Hd), 7.93 (2Hm), 8.7 (1Hd), 10.15 (1Hs), 13.01 (1H br s).
- (ii) N-[4-(4,7-dimethoxy-1H-benzimidazol-2-yl sulphinyl)-3-(2-pyridyl)phenyl]acetamide MW (fast atom bombardment) 437 (M++1).

EXAMPLE 15

2-[2-(4-Methoxy-2-pyridyl)-phenyl sulphinyl]-1H-benzimidazole (a) 2-[2-(4-Methoxy-2-pyridyl)-phenyl thio]-1H-benzimidazole To an ice cold solution of 2-(1H-benzimidazol-2-yl thio(benzenamine (1.70 g) in dilute hydrochloric acid (11 ml) was added dropwise a solution of sodium nitrite (0.53 g) in water (5 ml), keeping the temperature below 0°. The reaction mixture was stirred at this temperature for 0.5 hours then added portionwise to a mixture of 4-methoxypyridine (42.40 g) and pyridine (0.57 g) stirring at 80° for 1 hour. The pyridines were distilled off, replaced with 880 ammonia which was in turn distilled off. The residue was treated with water, extracted into dichloromethane, washed, dried, evaporated and the residue was purified by flash column chromatography using ethyl acetate as eluant to give the sub-title product as a creamish foam, 0.20 g. M.S. m/e 333 (M+, 10%), 300 (M+-32, 8%), 216 (100%).

(b) 2-[2-(4-Methoxy-2-pyridyl)-phenyl sulphinyl]-1H-benzimidazole

The title compound was prepared, from the product of step (a) above (0.18 g) by the method of Example 13 (b), as a cream/yellow solid, 0.10 g. M.S. m/e 350 (M++1), 154 (100%), FAB m.s.

EXAMPLE 16

2-[2-(2-Pyridyl)-phenyl methylsulphinyl]-1H-benzimidazole (a) 2-(2-Pyridyl)-benzenemethanol 2-Aminobenzylalcohol (10 g) was dissolved in concentrated hydrochloric acid (25 ml) and the solution diluted with water (20 ml). The solution was stirred at 0° and a solution of sodium nitrite (5.9 g) in water (20 ml) added dropwise. The mixture was stirred at 0° for 40 minutes. The solution was added dropwise to pyridine (92 ml) stirred at 80°. After stirring at 80° for 90 minutes the mixture was concentrated in vacuo and the residue heated with 880 ammonia (100 ml). The mixture was concentrated in vacuo and the residue slurried with water and extracted with ethyl acetate. The ethyl acetate was washed with brine, dried and evaporated. Flash chromatography produced the sub-title compound as a red oil (3.8 g). M.S. m/e 185 Base Peak 80.

(b) 2-[2-(2-Pyridyl)-phenyl methylthio]-1H-benzimidazole

To a stirred solution of the product of step (a) above (1.5 g) in dry benzene (50 ml) was added thionyl chloride (0.71 ml) dropwise. After stirring for 1 hour the solvent was removed in vacuo. The residue was dissolved in dry dimethylformamide (50 ml) and the solution treated with benzimidazole-2-thione (1.22 g) and potassium carbonate (2.24 g). The mixture was stirred for 4 hours then poured onto water (500 ml). After stirring for 30 minutes the precipitate was collected, washed with water and dried. Flash chromatography produced the sub-title compound as a dark brown glass (200 mg). NMR (CDCl3) delta 14.13 broad, 10.00 broad (1H), 8.81 (d.o.d. 1H), 7.98 (t.o.d. 1H), 7.93 (d,1H), 7.0–7.8 (m,9H), 4.45 (s,2H).

(c) 2-[2-(2-Pyridyl)-phenyl methylsulphinyl]-1H-benzimidazole

The product of step (b) above (169 mg) in ethyl acetate (10 ml) was cooled to −10° and treated with an ice cold solution of m-chloroperbenzoic acid (108 mg of 85%) in ethyl acetate (1 ml). The mixture was stirred for 50 minutes then washed with sodium bicarbonate solution, sodium bisulphite solution, water and brine and then dried and evaporated. Flash chromatography produced the title compound as a colourless solid (95 mg), mp 148°–150°.

EXAMPLE 17

1-Methyl-2-[2-(2-pyridyl)-phenyl sulphinyl]-1H-benzimidazole

2-[2-(2-Pyridyl)-phenyl sulphinyl]-1H-benzimidazole (Example 13) (0.7 g) in dry dimethylformamide (50 ml), methyl iodide (0.34 g) and anhydrous potassium carbonate (1.1 g) were stirred at room temperature for 1.75 hours. The mixture was poured onto water, extracted into ethyl acetate, washed, dried and evaporated under reduced pressure to leave the title compound as a cream solid (0.55 g).
Elemental Analysis
Found: C,67.48; H,4.54; N,12.60; S,9.62 $C_{19}H_{15}N_3OS$ 0.25 $H_2O$
Requires: C,67.48; H,4.59; N,12.40; S,9.47

EXAMPLE 18

5,6Diethoxy-2-[2-(2-pyridyl)-phenyl sulphinyl]-1H-benzimidazole

(a) 2-(2-Bromophenyl)pyridine

2-Bromobenzenamine (18.77 g) in 50 ml of conc HCl and 50 ml of water, was cooled in an ice bath and treated dropwise with stirring with a solution of sodium nitrite (8.28 g) in water (35 ml). After the addition was complete, the mixture was stirred in the ice bath for a further 30 minutes and then added portionwise (over 5 minutes) to pyridine (275 ml) stirred in an oil bath at 80° C. The mixture was heated (at 80° C.) for a further 1 hour, when the excess of pyridine was distilled off under reduced pressure. The residue was basified (aqueous sodium hydrogen carbonate) and extracted with ethyl acetate (3×). The extracts were washed with water (2×), dried (sodium sulphate) and evaporated to give a dark oil, which was flash chromatographed on silica using methylene chloride/ethyl acetate (20/1) as eluant. Pure sub-title compound (6.56 g) was obtained as a dark brown oil. m/z 235/233 (MW), 154 (Base Peak).

(b) 5,6-Diethoxy-2-[2-(2-pyridyl)-phenyl thio]-1H-benzimidazole 5,6-Diethoxy-2-mercaptobenzimidazole (1.0 g) was treated with powdered KOH (235 mg) in dimethylacetamide (15 ml). Half of the solvent was distilled off (to remove water). The mixture was cooled and the product of step (a) above (1.0 g) was added. The mixture was heated under reflux for 20 hours, cooled, poured into water, and acidified with HCl and rebasified with sodium hydrogen carbonate solution (pH approx 8).
The dark suspension was extracted with ethyl acetate (2×) and the extracts were washed with water (3×), filtered to remove some black insoluble material and dried (sodium sulphate) to give a dark oil which was flash chromatographed on silica. The sub-title compound was obtained as a brown oil 100 mg (6%) using neat ethyl acetate as eluant.
m/z 391, 362, 186 (Base Peak).

(c) 5,6-Diethoxy-2-[2-(2-pyridyl)-phenyl sulphinyl-1H-benzimidazole

The product of step (b) above was converted to the title compound by the method of Example 13 above, mp 194°–5°.

EXAMPLE 19

2-(5-Chloro-1H-benzimidazol-2-yl sulphinyl)-N,N,N',N'-tetramethyl-1,4-benzenediamine

(a) 2-(5-Chloro-1H-benzimidazol-2-yl thio)-N,N,N',N'-tetramethyl-1,4-benzenediamine N,N,N',N'-Tetramethyl-2,5-diaminophenyldisulphide (1.3 g) was dissolved in dry tetrahydrofuran (70 ml) and an ethereal solution of lithium aluminium hydride (5.0 ml of 1M) was added dropwise over 10 minutes. After stirring for 30 minutes. water was added dropwise until no further effervescence was observed. The mixture was poured onto dilute hydrochloric acid, basified with sodium bicarbonate solution and extracted with ethyl acetate. The ethyl acetate was washed with water and brine, and then dried and evaporated to leave a clear gum (940 g). The gum was dissolved in dry degassed dimethylformamide (50 ml) and a solution of 2,5-dichloro-1H-benzimidazole (0.9 g) in dry degassed dimethylformamide (30 ml) was added. The mixture was stirred and heated to 80° for 2 hours. The solvent was removed in vacuo and the residue triturated with water. The solid was collected and dissolved in dichloromethane. The solution was dried and the solvent removed in vacuo. Flash chromatography produced the sub-title compound as a gum which solidified on standing (550 mg).
MS MW 346/8 Base Peak 194.

(b) 2-(5-Chloro-1H-benzimidazol-2-yl sulphinyl)-N,N,N',N'-tetramethyl-1,4-benzenediamine The product of step (a) above (550 mg) was dissolved in ethyl acetate (20 ml) and cooled to −10°. A solution of m-chloroperbenzoic acid (320 mg of 85%) in ethyl acetate (5 ml) was cooled to 0° and added to the above solution. After stirring at below 0° for 3 hours the solution was washed with sodium bicarbonate solution, sodium metabisulphite solution, water and brine, and then dried and concentrated in vacuo. The residue was flash chromatographed to produce a yellow gum. Trituration with ether and petroleum ether produced the title compound as a pale yellow solid (125 mg), mp 161°–3°.

EXAMPLE 20

Phenylmethyl 2-[2-(2-pyridyl)-phenyl sulphinyl]benzimidazole-1-carboxylate

(a) Phenylmethyl 2-[2-(2-pyridyl)-phenyl thio]benzimidazole-1-carboxylate

2-[2-(2-Pyridyl)-phenyl thio]-1H-benzimidazole (0.825 mmole) in anhydrous dimethylformamide (15 ml) was treated under nitrogen with sodium hydride (0.90 mmole). The mixture was stirred for 20 minutes at room temperature, cooled to 5° and benzyl chloroformate (0.90 mmole) was added. The mixture was allowed to attain room temperature, then stirred for 18 hours after which it was poured into ice/water and extracted with ethyl acetate (2×15 ml). The combined extracts were washed with water, dried (MgSO4), filtered and evaporated to an oil. The oil was flash chromatographed on silica gel using 10% ethyl acetate in dichloromethane as eluant to give the sub-title compound as a brown oil, MW 437 Base Peak 91.

(b) Phenylmethyl 2-[2-(2-pyridyl)-phenyl sulphinyl]benzimidazole-1-carboxylate

Phenylmethyl 2-[2-(pyridyl)-phenyl thio]benzimidazole-1-carboxylate (0.41 mmole) in dry dichloromethane (10 ml) was treated at 0° with a solution of m-chloroperbenzoic acid (0.48 mmole) in dichloromethane (5 cm$^3$). The mixture was stirred for 3 hours at between 0° and 10° and then poured into aqueous sodium hydrogen carbonate. The organic phase was separated, dried (MgSO4), filtered and evaporated to give a pale brown foam. The foam was taken up into dichloromethane and flash chromatographed (4/1 CH2Cl2/60:80 petroleum ether) to give the title compound as a yellow gum.
FAB MW 454 (+1).

EXAMPLE 21

(a) Pellet Formulation
A pellet (220 mg) containing:

| a compound of formula I | 50 mg |
| lactose | 103 mg |
| starch | 50 mg |
| magnesium stearate | 2 mg |
| hydroxypropylcellulose | 15 mg |

(b) Capsule Formulation
A gelatin-shell hard capsule containing 350 mg of the core portion consisting of:

| a compound of formula I | 40 mg |
| lactose | 200 mg |
| starch | 70 mg |
| polyvinylpyrrolidone | 5 mg |
| crystalline cellulose | 35 mg |

(c) Granule Formulation
One gram of granules containing:

| a compound of formula I | 200 mg |
| lactose | 450 mg |
| corn starch | 300 mg |
| hydroxypropylcellulose | 50 mg |

We claim:
1. Compounds of formula I,

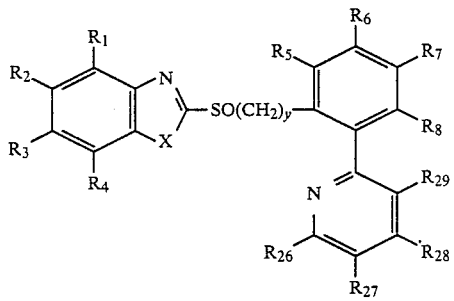

in which $R_1$ to $R_8$ and $R_{26}$ to $R_{29}$, which can be the same or different, are each hydrogen, halogen, phenoxy, alkyl $C_1$ to $C_6$, fluoralkyl $C_1$ to $C_6$, alkanoyl $C_1$ to $C_6$, benzoyl, $RS(O)_n-$, $NO_2$, $NRR_{14}$, NHCOR, —COOH or an ester with a $C_1$-$C_6$ alkanol or an unsubstituted or a mono- or di-($C_1$ to $C_6$ alkyl) substituted amide thereof, or alkoxy $C_1$ to $C_6$, and in addition, an adjacent pair of $R_1$, $R_2$, $R_3$, $R_4$, $R_5$, $R_6$, $R_7$, and $R_8$ may together form a chain —CH=CH—CH=CH—, y is 0 or 1,
n is 0, 1 or 2,
X is S, O, or $NR_{15}$,
$R_{15}$ is hydrogen, COOR or alkyl $C_1$ to $C_6$,
R and $R_{14}$, which can be the same or different, are each hydrogen, alkyl $C_1$ to $C_6$, alkyl $C_1$ to $C_6$ substituted by phenyl, or phenyl substituted by alkyl $C_1$ to $C_6$, or a pharmaceutically acceptable salt thereof.

2. A compound according to claim 1 which is 2-[2-(4-Methoxy-2-pyridyl)-phenyl sulphinyl]-1H-benzimidazole, or a pharmaceutically acceptable salt thereof.

3. A compound according to claim 1 and selected from

2-[2-(2-Pyridyl)-phenyl sulphinyl]-1H-benzimidazole,
5-Chloro-2-(2-(2-pyridyl)-phenylsulphinyl)-1H-benzimidazole,
2-[2-(2-Pyridyl)-phenyl sulphinyl]-benzothiazole,
Methyl 2-(2-(2-pyridyl)-phenyl sulphinyl)-1H-benzimidazole-5-carboxylate,
4-Trifluoromethyl-2-[2-(2-pyridyl)-phenyl sulphinyl]-1H-benzimidazole,
2-[2-(2-Pyridyl)-phenyl sulphinyl]-naphtho[2,3-d]imidazole,
2-[5-Chloro-2-(2-pyridyl)-phenyl sulphinyl]-5-methoxy-1H-benzimidazole,
5,6-Dimethyl-2-[2-(2-pyridyl)-phenyl sulphinyl]-1H-benzimidazole,
5-Methyl-2-[2-(2-pyridyl)-phenyl sulphinyl]-1H-benzimidazole,
5-(4-Methylphenylsulphonyl)-2-[2-(2-pyridyl)-phenyl sulphinyl]-1H-benzimidazole,
N-[4-(4,7-dimethoxy-1H-benzimidazol-2-yl sulphinyl)-3-(2-pyridyl)-phenyl]acetamide,
2-[2-(2-Pyridyl)-phenyl methylsulphinyl]-1H-benzimidazole,
1-Methyl-2-[2-(2-pyridyl)-phenyl sulphinyl]-1H-benzimidazole,
5,6-Diethoxy-2-[2-(2-pyridyl)-phenyl sulphinyl]-1H-benzimidazole,
Phenylmethyl 2-[2-(2-pyridyl)-phenyl sulphinyl]benzimidazole-1-carboxylate,
2-[2-(2-Pyridyl)-phenyl sulphinyl]-benzoxazole,
Phenyl [2-[2-(2-pyridyl)-phenyl sulphinyl]-1H-benzimidazol-5-yl]methanone,
5-Nitro-2-[4-nitro-2-(2-pyridyl)-phenyl sulphinyl]-1H-benzimidazole.

4. A pharmaceutical formulation for use as a cytoprotective agent, for inhibition of gastric acid secretion or for treatment of inflammatory conditions in mammals comprising an effective amount of the compound in accordance with claim 1 in admixture with a pharmaceutically acceptable adjuvant, diluent, or carrier.

5. A method for inhibiting gastric acid secretion which comprises administering an effective amount of a compound in accordance with claim 1 to a patient requiring such treatment.

6. A method for prophylaxis or treatment of an inflammatory condition which comprises administering an effective amount of a compound in accordance with claim 1 to a patient requiring such prophylaxis or treatment.

* * * * *